United States Patent [19]

Couderc et al.

[11] 4,036,888
[45] July 19, 1977

[54] PROCESS FOR THE PRODUCTION OF HYDROXY-PIVALDEHYDE

[75] Inventors: Pierre Couderc, Bethune; Serge Hilmoine, Aire-sur-la-Lys, both of France

[73] Assignee: Societe Chimique des Charbonnages, Paris, France

[21] Appl. No.: 625,074

[22] Filed: Oct. 23, 1975

[30] Foreign Application Priority Data

Oct. 30, 1974 France ............................. 74.36346

[51] Int. Cl.² .................................................. C07C 47/26
[52] U.S. Cl. ................................................... 260/602
[58] Field of Search ........................................ 260/602

[56] References Cited
U.S. PATENT DOCUMENTS

| | | | |
|---|---|---|---|
| 2,863,878 | 12/1958 | Lynn | 260/602 |
| 3,865,850 | 2/1975 | Merger | 260/602 |
| 3,876,706 | 4/1975 | Levanevsky et al. | 260/602 |
| 3,935,274 | 1/1976 | Jacobsen et al. | 260/602 |

Primary Examiner—James O. Thomas, Jr.
Assistant Examiner—W. B. Lone
Attorney, Agent, or Firm—Millen & White

[57] ABSTRACT

A process for the production of hydroxy-pivaldehyde which comprises reacting formaldehyde with isobutyraldehyde in an approximate molar ratio of 1:2 in the presence of a catalytic amount of triethylamine, to produce a reaction mixture containing 42 to 50 wt% of hydroxy-pivaldehyde, 28 to 35 wt% of isubutyraldehyde, approximately 18 wt% of water, approximately 2 wt% of triethylamine, and approximately 18 wt% of secondary reaction products, and recovering hydroxy-pivaldehyde therefrom. The recovery steps include adding at least one part by weight of water to 1 part of the solution, distilling the solution obtained under reduced pressure at a temperature below 65° C, to produce a distillate containing isobutyraldehyde, triethylamine and water, and an aqueous solution containing hydroxy-pivaldehyde, cooling the aqueous solution containing hydroxy-pivaldehyde, cooling the aqueous solution containing hydroxy-pivaldehyde to approximately 15° to 20° C to cause the crystallization of hydroxy-pivaldehyde, filtering off the crystals obtained, washing the crystals with cold water and then drying the crystals in air, and subjecting the mother liquors from the crystallization to liquid-liquid extraction at ambient temperature using approximately one volume of isobutyraldehyde to 3 volumes of the mother liquor.

8 Claims, 1 Drawing Figure

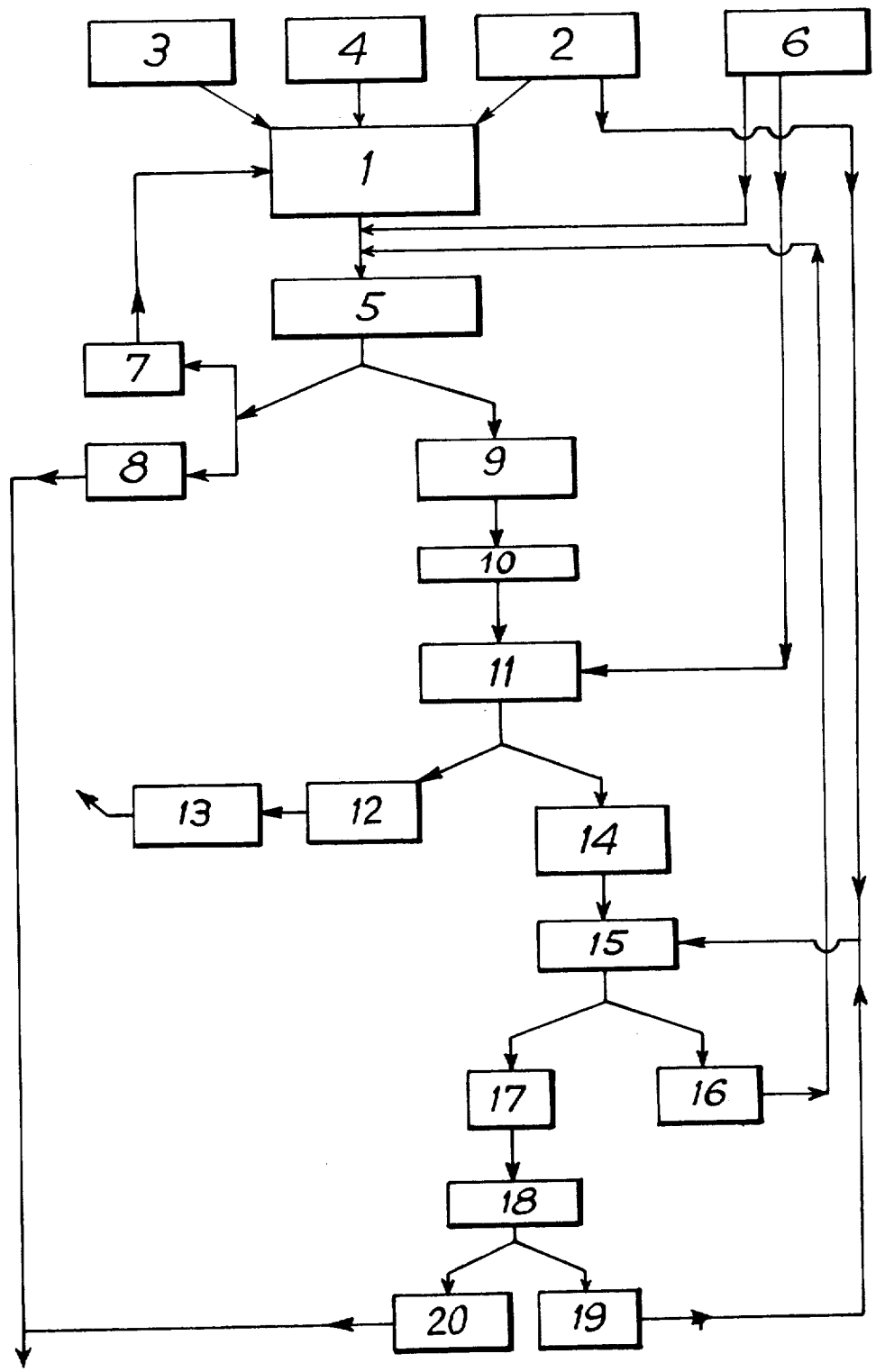

PROCESS FOR THE PRODUCTION OF HYDROXY-PIVALDEHYDE

This invention relates to processes for the production of hydroxy-pivaldehyde.

It has been priviously proposed to produce hydroxy-pivaldehyde by condensing isobutyraldehyde with formaldehyde; such reactions use a basic catalyst, which may be a hydroxide, an alkali metal carbonate, or an amine such as triethylamine.

According to the present invention there is provided a process for the production of hydroxy-pivaldehyde which comprises reacting formaldehyde with isobutyraldehyde in an approximate molar ratio of 1:2 in the presence of a catalytic amount of triethylamine, to produce a reaction mixture containing 42 to 50wt% of hydroxy-pivaldehyde, 28 to 35wt% of isobutyraldehyde, approximately 18wt% of water, approximately 2wt% of triethylamine, and approximately 2wt% of secondary reaction products, and recovering hydroxy-pivaldehyde therefrom, the recovering being effected by, a. adding at least one part of weight of water to 1 part by weight of the solution, distilling the solution obtained under reduced pressure at a temperature below 65° C, to produce a distillate containing isobutyraldehyde, triethylamine and water, and an aqueous solution containing hydroxy-pivaldehyde, b. cooling the aqueous solution containing hydroxy-pivaldehyde to approximately 15° to 20° C to cause the crystallization of hydroxy-pivaldehyde, filtering off the crystals obtained, washing the crystals with cold water and then drying the crystals in air, and c. subjecting the mother liquors from the crystallisation to liquid-liquid extraction at ambient temperature using approximately one volume of isobutyraldehyde to 3 volumes of the mother liquor.

It is preferred to react the isobutyraldehyde with the formaldehyde in solution in approximately 40% of water, in the presence of approximately 0.05 mol of triethylamine. The temperature of the reaction is preferably approximately 70° C, which enables all the formaldehyde to be reacted without obtaining more than 1 to 4% of secondary products such as esters and amine salts, based on the hydroxy-pivaldehyde.

The solution produced should have the following approximate composition:
42 to 50wt% of hydroxy-pivaldehyde,
28 to 35wt% of isobutyraldehyde,
approximately 18wt% of water,
approximately 2wt% of triethylamine,
and approximately 2wt% of secondary products.

The distillation is advantageously effected with at least 59% of water being present in the solution which is to be distilled, under a reduced pressure of 100 to 200 mm. of mercury, and in this way the temperature of the heated mixture does not exceed 65° C.

Distillation under reduced pressure provides a distillate consisting of water, isobutyraldehyde and triethylamine. The distillate is then cooled, the aqueous phase which forms is separated and the organic phase which forms can be returned to the reactor used for the synthesis of more hydroxy-pivaldehyde.

The concentrate resulting from the distillation consists essentially of water and hydroxy-pivaldehyde, but less than 0.2% of triethylamine. The concentrate is cooled at approximately 15° C so that hydroxy-pivaldehyde precipitates as crystals. These crystals are separated, washed with cold water, and dried in air. An industrial-grade hydroxy-pivaldehyde, having a melting point of 92° C and a degree of purity of approximately 97%, is obtained in this manner.

The crystallization is effected at a temperature of 15° C. However, at this temperature not all the hydroxy-pivaldehyde in the concentrate is recovered since the solubility of hydroxy-pivaldehyde in water at 20° C is approximately 5%. Consequently, hydroxy-pivaldehyde is recovered from the mother liquors. This recovery is effected by liquid-liquid extraction using isobutyraldehyde as the extractant and it is of interest because it results in no other chemical substance being fed into the process. Liquid-liquid extraction is therefore performed using isobutyraldehyde, preferably at a temperature of approximately 20° C, and it is possible to extract all the hydroxy-pivaldehyde present in approximately 3 volumes of mother liquor using one volume of isobutyraldehyde.

This liquid-liquid extraction produces an organic phase (isobutyraldehyde and hydroxy-pivaldehyde), which can be recycled to the reactor; the extraction also produces an aqueous phase containing a small quantity of isobutyraldehyde (approximately 4 to 5%). This isobutyraldehyde can be recovered by distillation.

A process for recovering not only hydroxy-pivaldehyde but also products of value (isobutyraldehyde and amine) can thus be achieved.

The accompanying drawing diagrammatically illustrates a recovery plant for effecting a process employing the present invention.

An example of a process employing the present invention will now be described with reference to the accompanying drawing. All parts are by weight unless otherwise stated.

A synthesis reactor 1 was supplied with the following reactants:
663 parts of freshly distilled isobutyraldehyde 2
314 parts of preferably de-acidified 44% formaldehyde 3
23 parts of triethylamine 4

The temperature of this mixture was gradually raised to 70° C while stirring, and this temperature was maintained for an hour. The solution was then cooled to 20° C. The resulting solution had the following composition:
approximately 46% of hydroxy-pivaldehyde,
approximately 32% of isobutyraldehyde,
17.5% of water,
2% of triethylamine,
1.5% of byproducts (ester and amine).

This solution was then transferred to a distillation plant 5, and approximately 1.25 parts of water per part of solution were added thereto during this transfer. This distilled or doubly demineralized water came from tank 6.

Distillation was effected under a pressure of 150 mm of mercury. The temperature in the boiler rose gradually from 40° to 64° C, and at the top of the tower from 22° to 60.5° C. The distillation was stopped when the temperature at the top of the tower reached 60.5° C.

After cooling, the distillate obtained separated into two phases, an organic phase and an aqueous phase. A concentrate was also obtained. The orgainc phase of the distillate 7 had the following composition:
isobutyraldehyde 88 – ρ%
hydroxy-pivaldehyde less than 0.2% triethylamine 2 to 5%
water 2.5 to 3%
and could be used again directly in reactor 1.

The aqueous phase of the distillate 8 was eliminated. The concentrate had the following composition:
water 67 to 75%
hydroxy-pivaldehyde 23 to 30%
isobutyraldehyde less than 0.1%
triethylamine less than 0.1%

This concentrate 9 was then cooled at a temperature of aproximately 15° to 20° C while stirring, and it was then filtered 10.

The crystals obtained are washed 11 – 12 and then dried 13 by fluidization in a flow of warm air (temperature 40° – 45° C).

The mother liquors 14 contained between approximately 4 and 6% of hydro-pivaldehyde and they were processed in an extractor 15 using isobutyraldehyde. This extraction was performed at 20° C using 290 parts of isobutyraldehyde to 1000 parts of mother liquor. The extractor had two or three stages only, since the coefficient of separation of hydroxy-pivaldehyde with isobutyraldehyde is very high.

This liquid-liquid extraction rendered it possible to obtain:
an organic phase 16 which was recycled, and which contains:
isobutyraldehyde, 72 to 75%
hydroxy-pivaldehyde, 13 to 16%
water, approximately 3.5%
impurities, from 0.8 to 2.5%
an aqueous phase 17 containing approximately 5 to 6% of isobutyraldehyde and which may be in known manner 18 so as to recover isobutyraldehyde which is recycled 19, and residual liquors 20 which are eliminated.

We claim:

1. A process for the recovery of hydroxy-pivaldehyde from a mixture containing 42 to 50wt% of hydroxy-pivaldehyde, 28 to 35wt% of isobutyraldehyde, approximately 18wt% of water, approximately 2wt% of triethylamine, and approximately 2wt% of secondary reaction products, said mixture produced by reacting formaldehyde with isobutyraldehyde in an approximate molar ratio of 1:2 in the presence of a catalyst amount of triethylamine, the formaldehyde being in the form of about 40% aqueous solution, the reaction being conducted at a sufficient temperature and for a sufficient time to produce said reaction mixture, the recovery comprising:

a. adding at least one part by weight of water to 1 part of the reaction mixture, distilling the solution obtained under reduced pressure at a temperature below 65° C, to produce a distillate containing isobutyraldehyde, triethylamine and water, and a concentrate of an aqueous solution containing hydroxy-pivaldehyde, b. cooling the concentrate of the aqueous solution containing hydroxy-pivaldehyde to approximately 15° to 20° C to cause the crystallization of hydroxy-pivaldehyde, filtering off the resultant crystals from the mother liquor, washing the crystals with cold water and then drying the crystals in air, and c. subjecting the mother liquor from the crystallization to liquid-liquid extraction at ambient temperature using approximately one volume of isobutyraldehyde to 3 volumes of the mother liquor to extract additional hydroxy-pivaldehyde.

2. A process according to claim 1, wherein the aqueous phase from the liquid-liquid extraction is distilled to recover isobutyraldehyde.

3. A process according to claim 1, wherein the distillate from step (a) is decanted to provide an aqueous phase which is eliminated, and an organic phase which is used for the synthesis of hydroxy-pivaldehyde.

4. A process according to claim 1 wherein the organic phase from the liquid-liquid extraction is fed with the said mixture to the said (a) operation step.

5. A process according to claim 1, said distilling being conducted at 100–100 mm Hg.

6. A process according to claim 1, said distilling being conducted at 150 mm Hg.

7. A process according to claim 1 wherein said reacting of formaldehyde with isobutyraldehyde is conducted at approximately 70° C.

8. A process according to claim 5, wherein said reacting of formaldehyde with isobutyraldehyde is conducted at approximately 70° C.